(12) United States Patent
Assaf et al.

(10) Patent No.: US 11,534,149 B2
(45) Date of Patent: Dec. 27, 2022

(54) APPARATUS FOR DELIVERING A DEVICE TO A HOLLOW ORGAN

(71) Applicant: Colospan Ltd., Kfar-Saba (IL)

(72) Inventors: Boaz Assaf, Hod-HaSharon (IL); Eyal Teichman, Hod HaSharon (IL); Shany Krimberg-Barel, Haifa (IL)

(73) Assignee: Colospan Ltd., Kfar-Saba (IL)

( * ) Notice: Subject to any disclaimer, the term of this patent is extended or adjusted under 35 U.S.C. 154(b) by 503 days.

(21) Appl. No.: 16/744,286

(22) Filed: Jan. 16, 2020

(65) Prior Publication Data

US 2020/0146663 A1    May 14, 2020

Related U.S. Application Data

(63) Continuation of application No. 15/505,253, filed as application No. PCT/IL2015/051021 on Oct. 13, 2015, now abandoned.

(Continued)

(51) Int. Cl.
*A61B 17/00* (2006.01)
*A61B 17/12* (2006.01)
(Continued)

(52) U.S. Cl.
CPC .... *A61B 17/00234* (2013.01); *A61B 17/1204* (2013.01); *A61B 17/12036* (2013.01);
(Continued)

(58) Field of Classification Search
CPC ........ A61B 17/00234; A61B 17/12036; A61B 17/1204; A61B 17/12099;
(Continued)

(56) References Cited

U.S. PATENT DOCUMENTS

| 3,435,823 | A | 4/1969 | Edwards |
| 3,828,782 | A | 8/1974 | Polin |

(Continued)

FOREIGN PATENT DOCUMENTS

| CA | 2670302 | 1/2010 |
| CN | 101883539 | 11/2010 |

(Continued)

OTHER PUBLICATIONS

Notice of Reasons for Rejection dated Jun. 9, 2020 From the Japan Patent Office Re. Application No. 2019-192859 and Its Translation Into English. (7 Pages).

(Continued)

*Primary Examiner* — Richard G Louis

(57) ABSTRACT

An apparatus for delivery of a device into a hollow organ and a method of delivery are provided. The apparatus includes an elongated tube having proximal and distal openings and being configured for carrying the device on a distal portion thereof. The apparatus further includes a tubular cover for covering at least a portion of the device when mounted on the elongated tube, the tubular cover being radially elastic and axially non-elastic. The tubular cover is retrievable into the elongated tube through the distal opening, such that when the device is mounted on the elongated tube and covered by the tubular cover, retrieval of the tubular cover into the elongated tube uncovers the device for delivery into the hollow organ.

13 Claims, 16 Drawing Sheets

Related U.S. Application Data

(60) Provisional application No. 62/063,421, filed on Oct. 14, 2014.

(51) Int. Cl.
    *A61M 25/04*     (2006.01)
    *A61M 27/00*     (2006.01)
    *A61B 17/11*     (2006.01)
    *A61F 2/04*     (2013.01)

(52) U.S. Cl.
    CPC .. *A61B 17/12099* (2013.01); *A61B 17/12136* (2013.01); *A61M 25/04* (2013.01); *A61M 27/002* (2013.01); *A61B 17/1114* (2013.01); *A61B 2017/00336* (2013.01); *A61B 2017/1132* (2013.01); *A61B 2017/1205* (2013.01); *A61F 2002/045* (2013.01); *A61F 2230/0065* (2013.01); *A61F 2250/0003* (2013.01)

(58) Field of Classification Search
    CPC .......... A61B 17/12136; A61B 17/1114; A61B 2017/00336; A61B 2017/1132; A61B 2017/1205; A61M 25/04; A61M 27/002; A61F 2002/045; A61F 2230/0065; A61F 2250/0003
    See application file for complete search history.

(56) References Cited

U.S. PATENT DOCUMENTS

| | | | |
|---|---|---|---|
| 4,368,739 A | 1/1983 | Nelson, Jr. | |
| 4,573,966 A | 3/1986 | Weikl et al. | |
| 4,905,693 A | 3/1990 | Ravo | |
| 5,007,437 A | 4/1991 | Sterzer | |
| 5,074,868 A | 12/1991 | Kuzmak | |
| 5,152,277 A | 10/1992 | Honda et al. | |
| 5,443,445 A | 8/1995 | Peters et al. | |
| 5,545,171 A | 8/1996 | Sharkey et al. | |
| 5,569,216 A | 10/1996 | Kim | |
| 5,620,457 A | 4/1997 | Pinchasik et al. | |
| 5,634,901 A | 6/1997 | Alba et al. | |
| 5,820,595 A | 10/1998 | Parodi | |
| 5,860,963 A | 1/1999 | Azam et al. | |
| 6,068,636 A | 5/2000 | Chen | |
| 6,082,855 A | 7/2000 | Fleming | |
| 6,254,611 B1 | 7/2001 | Vrba | |
| 6,299,598 B1 | 10/2001 | Bander | |
| 6,544,278 B1 | 4/2003 | Vrba et al. | |
| 6,575,932 B1 | 6/2003 | O'Brien et al. | |
| 6,576,429 B1 | 6/2003 | Haellgren | |
| 6,702,843 B1 | 3/2004 | Brown et al. | |
| 7,338,505 B2 | 3/2008 | Belson | |
| 7,387,640 B2 | 6/2008 | Cummings | |
| 7,846,132 B2 | 12/2010 | Gravesen et al. | |
| 8,216,159 B2 | 7/2012 | Leiboff | |
| 8,690,817 B2 | 4/2014 | Assaf et al. | |
| 2001/0007954 A1* | 7/2001 | Shaolian | A61F 2/07 623/1.11 |
| 2001/0049497 A1 | 12/2001 | Kalloo et al. | |
| 2002/0058955 A1 | 5/2002 | Blatter et al. | |
| 2002/0077594 A1 | 6/2002 | Chien et al. | |
| 2002/0077691 A1 | 6/2002 | Nachtigall | |
| 2002/0123786 A1 | 9/2002 | Gittings et al. | |
| 2002/0188282 A1 | 12/2002 | Greenberg | |
| 2003/0050662 A1 | 3/2003 | Don Michael | |
| 2003/0069472 A1 | 4/2003 | Butler | |
| 2003/0171775 A1 | 9/2003 | Belson | |
| 2003/0187428 A1 | 10/2003 | Lane et al. | |
| 2004/0153167 A1 | 8/2004 | Stack et al. | |
| 2004/0199240 A1 | 10/2004 | Dorn | |
| 2004/0243057 A1 | 12/2004 | Vinten-Johansen | |
| 2005/0033226 A1 | 2/2005 | Kim | |
| 2005/0038374 A1 | 2/2005 | Williams, Jr. et al. | |
| 2005/0080437 A1 | 4/2005 | Wright | |
| 2005/0085923 A1 | 4/2005 | Levine et al. | |
| 2005/0165426 A1 | 7/2005 | Manzo | |
| 2005/0197531 A1 | 9/2005 | Cabiri et al. | |
| 2005/0197664 A1 | 9/2005 | Blomme | |
| 2005/0209688 A1 | 9/2005 | Falotico et al. | |
| 2005/0277945 A1 | 12/2005 | Saadat et al. | |
| 2006/0030923 A1* | 2/2006 | Gunderson | A61F 2/95 623/1.11 |
| 2006/0167538 A1 | 7/2006 | Rucker | |
| 2007/0118157 A1 | 5/2007 | Zuidema et al. | |
| 2007/0208350 A1 | 9/2007 | Gunderson | |
| 2007/0250084 A1 | 10/2007 | Sharkawy et al. | |
| 2008/0039878 A1 | 2/2008 | Williams et al. | |
| 2008/0082159 A1 | 4/2008 | Tseng et al. | |
| 2008/0103442 A1 | 5/2008 | Kesten et al. | |
| 2008/0146869 A1 | 6/2008 | Chow et al. | |
| 2008/0183202 A1 | 7/2008 | Isham | |
| 2008/0221597 A1 | 9/2008 | Wallace et al. | |
| 2009/0048654 A1* | 2/2009 | Chmura | A61M 27/008 623/1.11 |
| 2009/0062608 A1 | 3/2009 | Miyoshi | |
| 2009/0062717 A1 | 3/2009 | Laufer | |
| 2009/0093767 A1 | 4/2009 | Kelleher | |
| 2009/0099546 A1 | 4/2009 | Macy, Jr. | |
| 2009/0149880 A1 | 6/2009 | Gobel | |
| 2009/0216337 A1 | 8/2009 | Egan et al. | |
| 2009/0270955 A1 | 10/2009 | Magers et al. | |
| 2009/0275889 A1 | 11/2009 | Ravikumar | |
| 2009/0326490 A1 | 12/2009 | McMichael et al. | |
| 2010/0010519 A1 | 1/2010 | Stopek et al. | |
| 2010/0016871 A1 | 1/2010 | Brooks et al. | |
| 2010/0022976 A1 | 1/2010 | Weig | |
| 2010/0023132 A1 | 1/2010 | Imran | |
| 2010/0076470 A1 | 3/2010 | Elachchabi et al. | |
| 2010/0105983 A1 | 4/2010 | Oneda et al. | |
| 2010/0125280 A1 | 5/2010 | Molloy | |
| 2010/0191264 A1 | 7/2010 | Kassab et al. | |
| 2010/0256775 A1 | 10/2010 | Belhe et al. | |
| 2010/0268154 A1 | 10/2010 | Vining | |
| 2010/0274349 A1 | 10/2010 | Lord et al. | |
| 2010/0286717 A1 | 11/2010 | Heinrich et al. | |
| 2010/0286753 A1 | 11/2010 | Zelickson et al. | |
| 2010/0305503 A1 | 12/2010 | Fang et al. | |
| 2010/0312272 A1 | 12/2010 | Pavcnik et al. | |
| 2011/0009690 A1 | 1/2011 | Belhe et al. | |
| 2011/0015571 A1 | 1/2011 | Voss et al. | |
| 2011/0034987 A1* | 2/2011 | Kennedy | A61F 2/9662 623/1.11 |
| 2011/0040231 A1 | 2/2011 | Gregory | |
| 2011/0118817 A1* | 5/2011 | Gunderson | A61F 2/95 623/1.12 |
| 2011/0137428 A1 | 6/2011 | Terliuc | |
| 2011/0160657 A1 | 6/2011 | Goebel | |
| 2011/0172584 A1 | 7/2011 | Chin | |
| 2011/0208139 A1 | 8/2011 | Kim et al. | |
| 2011/0218493 A1 | 9/2011 | Miyasaka et al. | |
| 2011/0245752 A1 | 10/2011 | Levine et al. | |
| 2011/0295288 A1* | 12/2011 | Khosrovaninejad | A61B 17/1114 606/153 |
| 2011/0306823 A1 | 12/2011 | Goebel et al. | |
| 2012/0078029 A1 | 3/2012 | Subramanian | |
| 2012/0095432 A1 | 4/2012 | Nath | |
| 2012/0232459 A1 | 9/2012 | Dann et al. | |
| 2012/0239076 A1 | 9/2012 | Cisko, Jr. | |
| 2012/0253204 A1 | 10/2012 | Ben-Yehuda | |
| 2012/0310138 A1 | 12/2012 | Behan | |
| 2013/0158463 A1 | 6/2013 | Assaf et al. | |
| 2014/0163312 A1 | 6/2014 | Goebel | |
| 2014/0188029 A1 | 7/2014 | Assaf et al. | |
| 2015/0045715 A1 | 2/2015 | Assaf et al. | |
| 2016/0074189 A1* | 3/2016 | Cummins | A61F 2/966 623/1.11 |

(56) References Cited

U.S. PATENT DOCUMENTS

| | | | |
|---|---|---|---|
| 2017/0087343 | A1 | 3/2017 | Assaf et al. |
| 2017/0265849 | A1 | 9/2017 | Assaf et al. |

FOREIGN PATENT DOCUMENTS

| | | |
|---|---|---|
| CN | 103370016 | 10/2013 |
| EP | 1298477 | 4/2003 |
| JP | 08-112359 | 5/1996 |
| JP | 09-038197 | 2/1997 |
| JP | 09-038198 | 2/1997 |
| JP | 2000-014767 | 1/2000 |
| JP | 2000-325483 | 11/2000 |
| JP | 2001-170164 | 6/2001 |
| JP | 2002-065595 | 3/2002 |
| JP | 2002-065844 | 3/2002 |
| JP | 2005-519709 | 7/2005 |
| JP | 2017-519820 | 7/2017 |
| WO | WO 03/086507 | 10/2003 |
| WO | WO 2007/059490 | 5/2007 |
| WO | WO 2007/140559 | 12/2007 |
| WO | WO 2009/046998 | 4/2009 |
| WO | WO 2012/081005 | 6/2012 |
| WO | WO 2012/148727 | 11/2012 |
| WO | WO 2016/059634 | 4/2016 |

OTHER PUBLICATIONS

Decision of Rejection dated Dec. 1, 2020 From the Japan Patent Office Re. Application No. 2019-192859 and Its Translation Into English. (2 Pages).
Advisory Action Before the Filing of an Appeal Brief dated Mar. 1, 2019 From the US Patent and Trademark Office Re. U.S. Appl. No. 15/505,253. (3 pages).
Advisory Action Before the Filing of an Appeal Brief dated Mar. 14, 2018 From the US Patent and Trademark Office Re. U.S. Appl. No. 14/521,482. (2 pages).
Decision of Rejection dated Aug. 16, 2019 From the Japan Patent Office Re. Application No. 2017-519820 and Its Translation Into English. (4 Pages).
Examination Report dated Aug. 1, 2019 From the Servi?o Publico Federal, Ministerio da Economia, Instituto Nacional da Propriedade Industrial do Brasil Re. Application No. BR112013014918-3. (4 Pages).
Examination Report Under Section 12 & 13 of the Patents Act, 1970 and the Patents Rules, 2003 dated Jul. 12, 2019 From the Government of India, Intellectual Property India, Patents, Designs, Trade Marks, Geographical Indications Re. Application No. 1046/MUMNP/2013. (6 Pages).
International Preliminary Report on Patentability dated Apr. 27, 2017 From the International Bureau of WIPO Re. Application No. PCT/IL2015/051021. (6 Pages).
International Preliminary Report on Patentability dated Jun. 27, 2013 From the International Bureau of WIPO Re. Application No. PCT/IL2011/000934.
International Search Report and the Written Opinion dated Sep. 16, 2016 From the International Searching Authority Re. Application No. PCT/IL2015/051021.
International Search Report and the Written Opinion dated May 21, 2012 From the International Searching Authority Re. Application No. PCT/IL2011/000934.
Notice of Reason for Rejection dated Feb. 2, 2016 From the Japanese Patent Office Re. Application No. 2013-543966.
Notice of Reason for Rejection dated Jul. 21, 2015 From the Japanese Patent Office Re. Application No. 2013-543966.
Notice of Reason for Rejection dated Jan. 31, 2017 From the Japanese Patent Office Re. Application No. 2013-543966 and Its Translation Into English. (4 Pages).
Notice of Reasons for Rejection dated May 14, 2019 From the Japan Patent Office Re. Application No. 2017-519820. (4 Pages).
Notification of Office Action and Search Report dated Jul. 15, 2015 From the State Intellectual Property Office of the People's Republic of China Re. Application No. 201180060468.4.
Notification of Office Action and Search Report dated Jun. 21, 2018 From the State Intellectual Property Office of the People's Republic of China Re. Application No. 201580052994.4 and Its Translation of Office Action Into English. (6 Pages).
Notification of Office Action dated Feb. 2, 2015 From The State Intellectual Property Office of the People's Republic of China Re. Application No. 201180060468.4 and Its Translation Into English.
Notification of Office Action dated Dec. 23, 2015 From The State Intellectual Property Office of the People's Republic of China Re. Application No. 201180060468.4 and Its Translation Into English.
Office Action dated Apr. 21, 2016 From the Israel Patent Office Re. Application No. 226843 and Its Translation Into English.
Office Action dated Apr. 27, 2017 From the Israel Patent Office Re. Application No. 226843 and Its Translation Into English. (5 Pages).
Official Action dated May 5, 2017 From the US Patent and Trademark Office Re. U.S. Appl. No. 15/289,216. (18 pages).
Official Action dated Sep. 10, 2013 From the US Patent and Trademark Office Re. U.S. Appl. No. 13/769,338.
Official Action dated Nov. 15, 2018 From the US Patent and Trademark Office Re. U.S. Appl. No. 15/505,253. (10 pages).
Official Action dated Jan. 17, 2019 From the US Patent and Trademark Office Re. U.S. Appl. No. 15/505,253. (9 pages).
Official Action dated May 23, 2013 From the US Patent and Trademark Office Re. U.S. Appl. No. 13/769,338.
Official Action dated Aug. 24, 2017 From the US Patent and Trademark Office Re. U.S. Appl. No. 14/521,482. (46 pages).
Official Action dated Sep. 25, 2019 From the US Patent and Trademark Office Re. U.S. Appl. No. 15/505,253. (19 pages).
Official Action dated Dec. 29, 2017 From the US Patent and Trademark Office Re. U.S. Appl. No. 14/521,482. (14 pages).
Official Action dated Jan. 29, 2016 From the US Patent and Trademark Office Re. U.S. Appl. No. 14/184,534.
Official Action dated Jun. 30, 2016 From the US Patent and Trademark Office Re. U.S. Appl. No. 14/184,534.
Official Action dated May 31, 2019 From the US Patent and Trademark Office Re. U.S. Appl. No. 15/505,253. (14 Pages).
Pre-Appeal Examination Report dated May 26, 2016 From the Japanese Patent Office Re. Application No. 2013-543966 and Its Translation Into English.
Restriction Official Action dated Jun. 8, 2018 From the US Patent and Trademark Office Re. U.S. Appl. No. 15/505,253. (9 pages).
Supplementary European Search Report and the European Search Opinion dated May 11, 2018 From the European Patent Office Re. Application No. 15850811.9. (8 Pages).
Supplementary European Search Report and the European Search Opinion dated Nov. 23, 2016 From the European Patent Office Re. Application No. 11848922.8. (10 Pages).
Translation Dated Aug. 5, 2015 of Notice of Reason for Rejection dated Jul. 21, 2015 From the Japanese Patent Office Re. Application No. 2013-543966.
Translation Dated Feb. 16, 2016 of Notice of Reason for Rejection dated Feb. 2, 2016 From the Japanese Patent Office Re. Application No. 2013-543966.
Translation Dated May 24, 2019 of Notice of Reasons for Rejection dated May 14, 2019 From the Japan Patent Office Re. Application No. 2017-519820. (3 Pages).
Translation of Notification of Office Action dated Jul. 15, 2015 From the State Intellectual Property Office of the People's Republic of China Re. Application No. 201180060468.4.
Office Action dated Jul. 23, 2020 From the Israel Patent Office Re. Application No. 251454 and Its Translation Into English. (5 Pages).

* cited by examiner

APPARATUS FOR DELIVERING A DEVICE TO A HOLLOW ORGAN

RELATED APPLICATIONS

This application is a continuation of U.S. patent application Ser. No. 15/505,253 filed on Feb. 21, 2017, which is a National Phase of PCT Patent Application No. PCT/IL2015/051021 having International Filing Date of Oct. 13, 2015, which claims the benefit of priority under 35 USC § 119(e) of U.S. Provisional Patent Application No. 62/063,421 filed on Oct. 14, 2014. The contents of the above applications are all incorporated by reference as if fully set forth herein in their entirety.

FIELD AND BACKGROUND OF THE INVENTION

The resent invention relates to an apparatus for delivering a device into a hollow organ. Embodiments of the present invention relate to an apparatus for delivering and deploying an intra-luminal sheath for bypassing an anastomosis site in a colon.

Surgical intervention can require an operative union of resected tissues or a bypass of non-resected diseased tissue. Such union procedures, which are termed anastomosis, can be performed via open or minimal invasive surgery where the ligated ends are manually sutured or stapled using a surgical stapler. While an anastomosis may be end-to-end, it could also be performed side-to-side or end-to-side depending on the required reconstruction or bypass. Anastomosis can be performed on vascular structures, the gastrointestinal (GI) tract (including esophagus, stomach, small bowel, large bowel, bile ducts, and pancreas), and the urinary tract (including ureters, urinary bladder and urethra).

Surgical anastomosis is a common procedure, in particular in the gastrointestinal (GI) tract. Virtually all elective resections of gastrointestinal organs are followed by anastomoses to restore continuity.

Although commonly performed, GI anastomosis carry a relatively high risk of anastomotic leaks especially in subjects that are immuno-compromised, such as subjects undergoing chemotherapy. Such leaks must be identified in a reasonable amount of time to allow for medical intervention.

In order to address the problem of anastomotic leaks, several internal sheaths which bypass the anastomotic site have been devised. Such sheaths are typically delivered via dedicated catheters and anchored above (upstream) the anastomotic site thereby supporting the flow of material to circumvent or bypass the anastomosis site.

Delivery of such devices to the anastomosis site requires precise positioning and deployment as well as effective anchoring without traumatizing the tissue.

While reducing the present invention to practice, the present inventors have devised an apparatus which can be used to deliver an intra-luminal sheath to the anastomosis site without causing tissue trauma during delivery or anchoring.

SUMMARY OF THE INVENTION

According to one aspect of the present invention there is provided an apparatus for delivery of a device into a hollow organ comprising: (a) an elongated tube having proximal and distal openings and being configured for carrying the device on a distal portion thereof; and (b) a tubular cover for covering at least a portion of the device when mounted on the elongated tube, the tubular cover being radially elastic and axially non-elastic; the tubular cover being retrievable into the elongated tube through the distal opening, such that when the device is mounted on the elongated tube and covered by the tubular cover, retrieval of the tubular cover into the elongated tube uncovers the device for delivery into the hollow organ.

According to further features in preferred embodiments of the invention described below, the apparatus further comprises an additional elongated tube positioned within the elongated tube and being attached to the tubular cover structure, wherein the tubular cover is retrievable into the elongated tube by pulling the additional elongated tube against the elongated tube.

According to still further features in the described preferred embodiments the elongated tube includes a hollow nose cone forming the distal opening.

According to still further features in the described preferred embodiments the tubular cover is fabricated from an elastic material having non-elastic axial elements.

According to still further features in the described preferred embodiments the elastic material is an elastic polymer.

According to still further features in the described preferred embodiments a proximal end of each of the elongated tube and the additional elongated tube is attached to a user-operable handle.

According to still further features in the described preferred embodiments the device is mounted on a distal portion of the elongated tube.

According to still further features in the described preferred embodiments the apparatus further comprises a fluid conduit for delivering friction-reducing composition to a distal portion of the elongated tube.

According to still further features in the described preferred embodiments the conduit is removably attached to the elongated tube.

According to still further features in the described preferred embodiments a distal opening of the fluid conduit is positioned such that the friction-reducing composition is delivered between the tubular cover and the device when the device is mounted on the elongated tube.

According to still further features in the described preferred embodiments the friction-reducing composition is an oil or a water-based lubricant.

According to another aspect of the present invention there is provided a method of delivering a device into a hollow organ comprising: (a) delivering into the hollow organ an elongated tube having proximal and distal openings, the elongated tube having the device mounted thereupon and being at least partially covered by a tubular cover being radially elastic and axially non-elastic; (b) retrieving the tubular cover into the elongated tube through the distal opening thereby uncovering the device; and (c) pulling the elongated tube in a proximal direction to thereby deliver the device to the hollow organ.

According to still further features in the described preferred embodiments the tubular cover is attached to an additional elongated tube positioned within the elongated tube and further wherein (b) is effected by pulling the additional elongated tube against the elongated tube.

According to still further features in the described preferred embodiments the tubular cover is fabricated from an elastic material having non-elastic axial elements.

According to still further features in the described preferred embodiments the device is a tubular sleeve having at least one toroidal balloon and further wherein the toroidal balloon is inflated to anchor the tubular sleeve in the hollow organ prior to, or following (c).

According to still further features in the described preferred embodiments the hollow organ is a colon and the tubular sleeve is at least 200 mm in length.

According to still further features in the described preferred embodiments the hollow organ is a colon and further wherein (a) is effected by delivering the tubular sleeve through the anal orifice.

According to still further features in the described preferred embodiments at least one toroidal balloon is inflated via an inflation conduit having an inflation port positioned outside the body.

According to still further features in the described preferred embodiments the method further comprising delivering a friction-reducing composition to a distal portion of the elongated tube prior to (b).

According to still further features in the described preferred embodiments the delivering is effected via a fluid conduit having a distal opening positioned at the distal portion of the elongated tube.

According to still further features in the described preferred embodiments a distal opening of the fluid conduit is positioned such that the friction-reducing composition is delivered between the tubular cover and the device.

According to still further features in the described preferred embodiments the friction-reducing is an oil or a water-based lubricant.

The present invention successfully addresses the shortcomings of the presently known configurations by providing a delivery apparatus that can be used to deliver a device into a hollow organ.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF SPECIFIC EMBODIMENTS OF THE INVENTION

Figure 1:
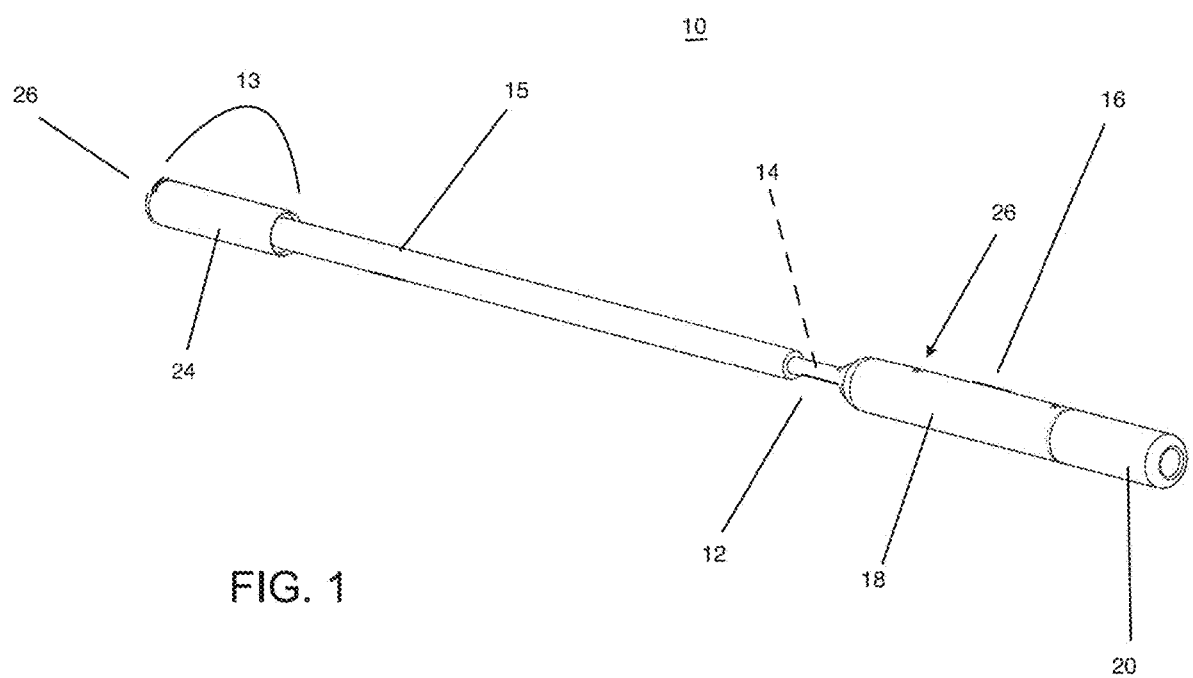
FIG. 1 illustrates the present delivery apparatus with an intraluminal device mounted thereupon and covered by a tubular cover.

The present invention is of an apparatus which can be used to deliver a device into a hollow organ. Specifically, the present invention can be used to deliver a device for bypassing an anastomosis site in a hollow organ such as a colon.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Leaks from anastomosis sites are a major complication of surgical union of hollow organ tissues. In fact, the rate and clinical implications of anastomotic leakage in colorectal and colo-anal anastomosis oftentimes necessitates a loop stoma for fecal diversion.

To address this problem, anastomosis protection devices for internally bypassing an anastomosis site have been developed. Such protection devices employ internally anchored sleeves (e.g. U.S. 20100010517, U.S. 20100010518) or externally clamped sleeves (e.g. U.S. Pat. No. 3,435,823, U.S. 20050033226) for routing feces and isolating it from the anastomosis site. Although bypass devices provide a promising alternative to fecal diversion procedures, they have yet to meet clinical acceptance largely due to complications associated with sleeve-tissue anchoring and sleeve placement and removal.

U.S. Pat. No. 8,690,817 to the present inventors discloses a unique anastomosis bypass device that includes several expandable toroidal balloons. The balloons stabilize the device against the inner walls of the colon and provide sealing thereagainst, while an externally mounted band (surrounding the colon) limits movement of the intraluminal device within the colon.

Experiments conducted by the present inventors have revealed that delivery of such an intraluminal device can be limited by less than optimal device unsheathing and deployment (see the Examples section for more detail).

In order to solve these problems and facilitate smooth delivery and deployment of the intraluminal device, the present inventors have devised a delivery apparatus which can be used to deliver and deploy an intraluminal device such as that described in U.S. Pat. No. 8,690,817.

Thus, according to one aspect there is provided an apparatus for delivery of a device into a hollow organ.

As used herein, the phrase "hollow organ" refers to any hollow tissue structure that serves as a conduit for biological material. Examples include the GI tract, including the esophagus, stomach and intestines, the urinary tract, including the ureters, bladder and urethra, and the vascular system including arteries, veins and the like. As used herein, the phrase biological material includes, but is not limited to, feces, urine, blood and the like.

The delivery apparatus of the present invention includes an elongated tube (also referred to herein as "outer tube") having proximal and distal openings; the outer tube is configured for carrying the deliverable device thereupon. The delivery apparatus further includes a tubular cover for covering at least a portion of the device when mounted on the outer tube. The tubular cover is retrievable into the outer tube through the distal opening, such that when the device is mounted on the outer tube and covered by the tubular cover, retrieval of the tubular cover into the outer tube uncovers the device for delivery into the hollow organ.

As is further described in the Examples section which follows, experiments conducted with various configurations of a tubular cover have revealed that the friction between the deliverable device and the tubular cover disposed therearound prevents efficient uncovering of the device due to a longitudinal stretching of the tubular cover in response to a pulling force. Such stretching resulted in a reduction of the diameter of the tubular cover and an increase in friction between the cover and delivered device that prevented device release.

In order to overcome these problems, the tubular cover of the present delivery apparatus was designed with radial elasticity and axially rigidity (inelasticity).

The radial elasticity enables the tubular cover to closely hug and apply compressive (packing) forces on the deliverable device or a portion thereof, while the longitudinal (axial) rigidity (non-elasticity) prevents longitudinal stretching of the tubular cover when pulled into the outer tube through the distal opening thereof.

The tubular cover is pulled into the outer tube by an additional elongated tube (also referred to herein as "inner tube") which is disposed within the outer tube and is attached to the distal portion of the tubular cover. Pulling of the inner tube with respect to the outer tube pulls the tubular cover in a distal direction into the distal opening of the outer tube thereby uncovering the distal portion of the outer tube (on which a deliverable device is mounted).

FIGS. 1-5 illustrate one embodiment of the present apparatus which is referred to herein as apparatus 10.

Apparatus 10 includes an outer tube 12 that is disposed over an inner tube 14 (not visible, indicated with dotted line). Outer tube 12 can be fabricated from PTFE, Nylon, Pebax, or any other thermoplastic/elastic polymer (with or without braid reinforcement), or a metal (e.g. stainless steel or Nitinol). Outer tube 12 can be thin (wall thickness of 0.5-1 mm or less) or slotted to allow flexibility and yet provide pushability. The outer diameter (OD) of outer tube 12 can be 3-7 mm while the inner diameter (ID) can be 2-6 mm. Outer tube can be fabricated via extrusion or any other suitable fabrication approach.

Inner tube 14 can be fabricated via, for example, extrusion using the materials described above. Inner tube 14 can have an OD of 2-6 mm and an ID of 0.1-1 mm.

Figure 3:
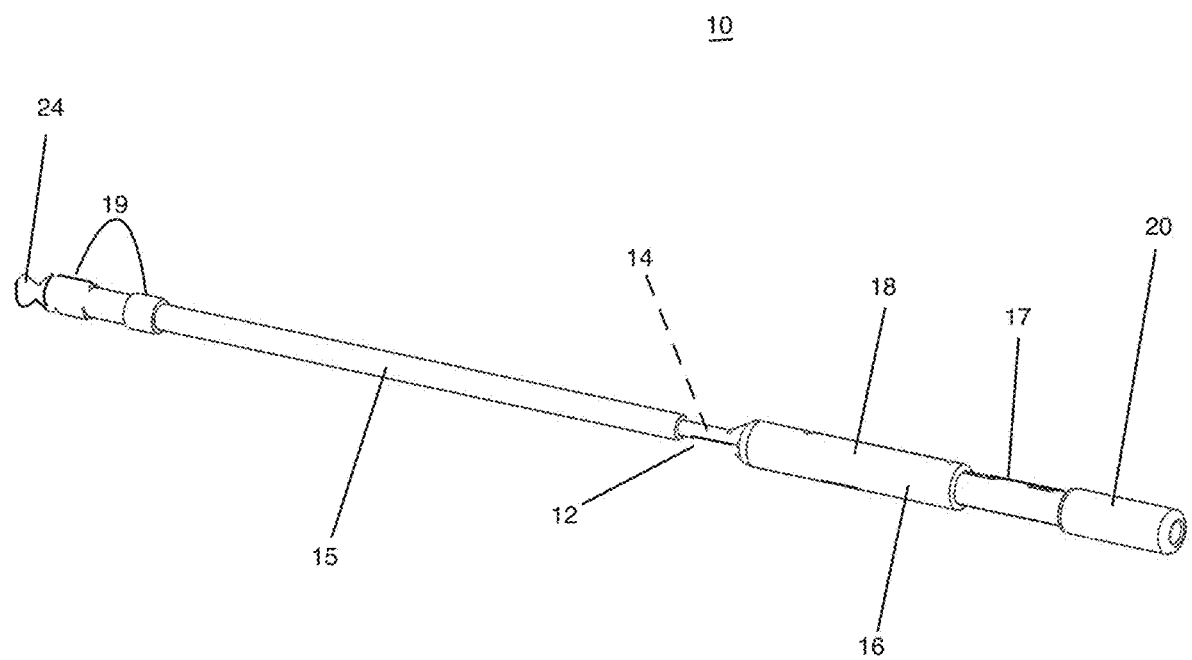
FIG. 3 illustrates the delivery apparatus of FIG. 1 with the intraluminal device mounted thereupon and the tubular cover partially withdrawn into the lumen of the delivery apparatus through the distal opening of the elongated (outer) tube.
Figure 5:
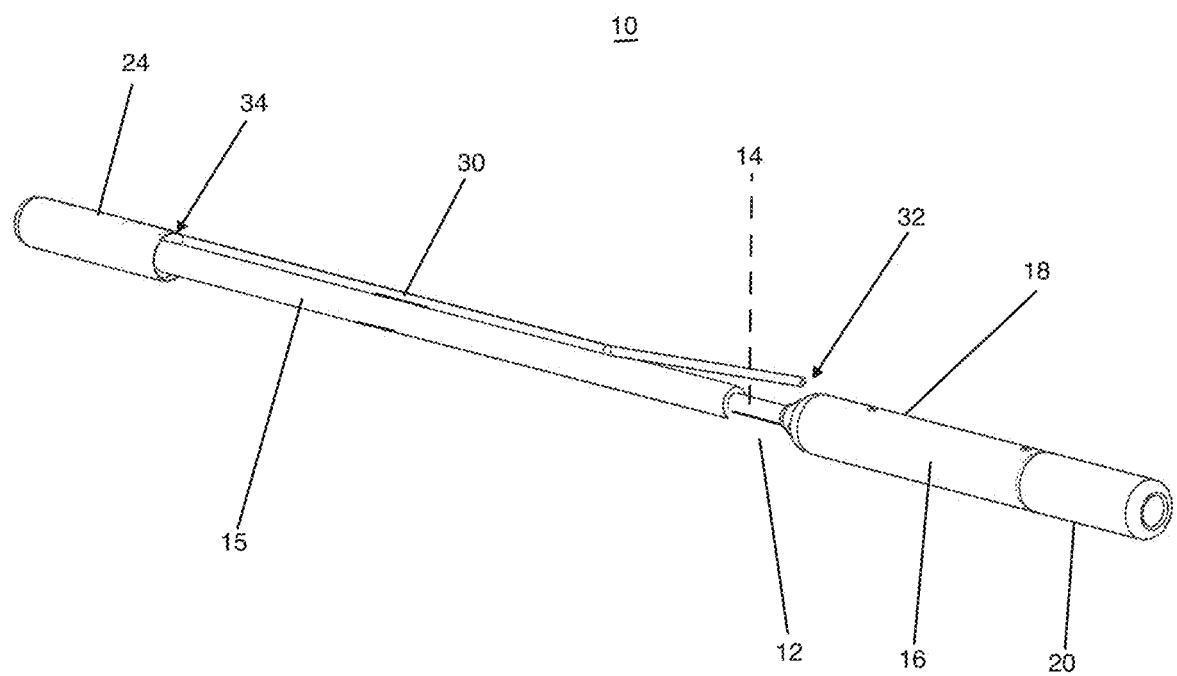
FIG. 5 illustrates a fluid a conduit for delivering a friction-reducing composition to the distal portion of the delivery apparatus.

At least a distal portion 13 of outer tube 12 is configured for carrying a deliverable device. Device 15 shown in FIGS. 1, 3 and 5 is configured for bypassing/shielding colon anastomosis sites and is about 200-500 cm in length. As such, device 15 is disposed over the length of outer tube 12, with only a tissue-anchoring segment thereof (having two toroidal anchoring balloons 19 shown in FIGS. 3 and 5) being covered by tubular cover 24. However, shorter devices can be mounted over distal portion 13 and be completely covered by tubular cover 24.

Apparatus includes handle 16 having two portions, a proximal portion 20 which is connected to inner tube 14 and a distal portion 18 which is connected to outer tube 12. Handle portion 18 and 20 can be fabricated via machining, 3D printing or molding using a variety of polymers and/or alloys (e.g. POM-C, ABS, polycarbonate, stainless steel etc.) Handle 16 can be 100-200 mm in length and 15-45 mm in diameter.

Proximal portion 20 can be pulled against distal portion 18 to thereby pull inner tube 14 with respect to outer tube 12. Handle 16 includes a safety mechanism 26 (e.g. a removable pin, a movable element, a ratchet mechanism or the like) for preventing inadvertent pulling of portion 20 with respect to portion 18 when apparatus 10 is used.

Distal end 22 of inner tube 14 is connected to a tubular cover 24 (FIG. 2a) which is configured for partially or fully covering a deliverable device (partial covering is shown with device 15 of FIG. 1). Pulling of portion 20 with respect to portion 18 pulls distal end 22 of inner tube 14 in a proximal direction and withdraws tubular cover 24 into outer tube 12 through opening 26 (FIG. 3). Tubular cover 24 can be partially or completely pulled into outer tube 12 (partial withdrawal into outer tube 12 shown in FIG. 3). A graduated scale 17 (FIGS. 3 and 4) disposed within handle 16 can become visible as portion 20 is pulled to indicate the portion (in percent or mm) of tubular cover withdrawn into outer tube 12.

Tubular cover 24 is a radially elastic, longitudinally rigid tubular structure which is capable of elastically stretching radially to accommodate device 15 and apply a compressive force thereupon.

Tubular cover 24 can be fabricated from nylon, silicone, latex, rubber, polyurethane or the like with a radial compliance of 10-100%. Fabrication can be effected using common approaches such as dipping, blow molding, casting, extrusion or the like.

Figure 2A:
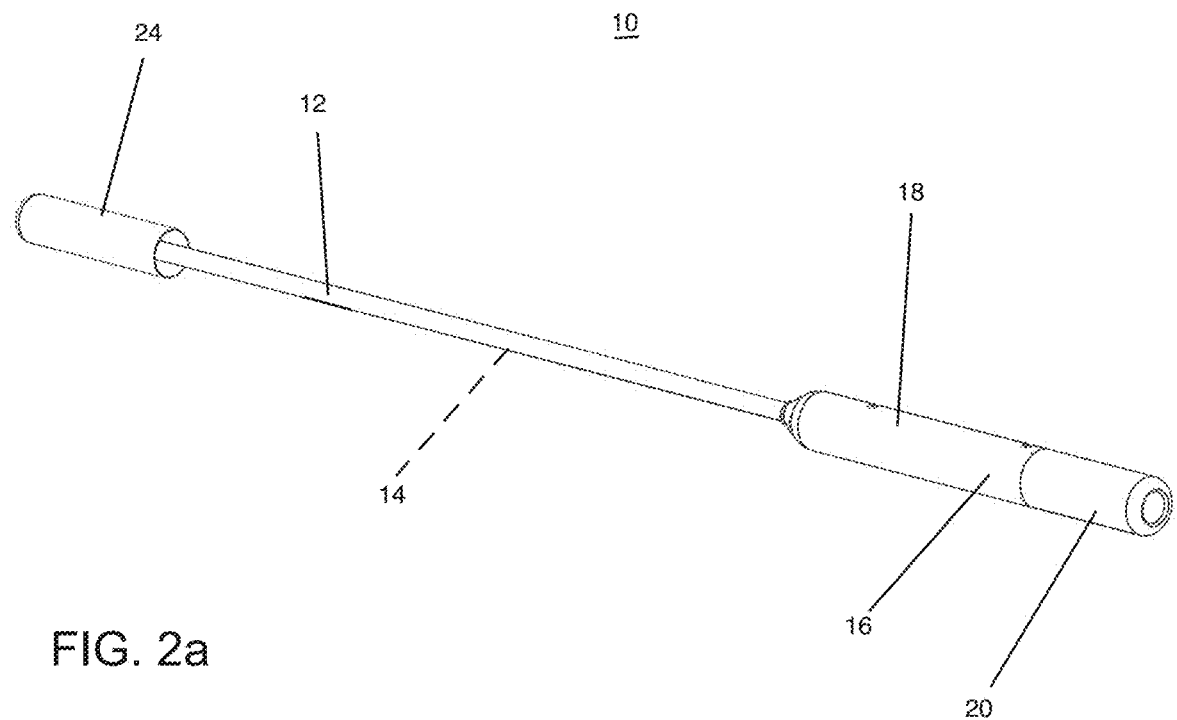
FIG. 2a illustrates the delivery apparatus of FIG. 1 without the intraluminal device.
Figure 2B:
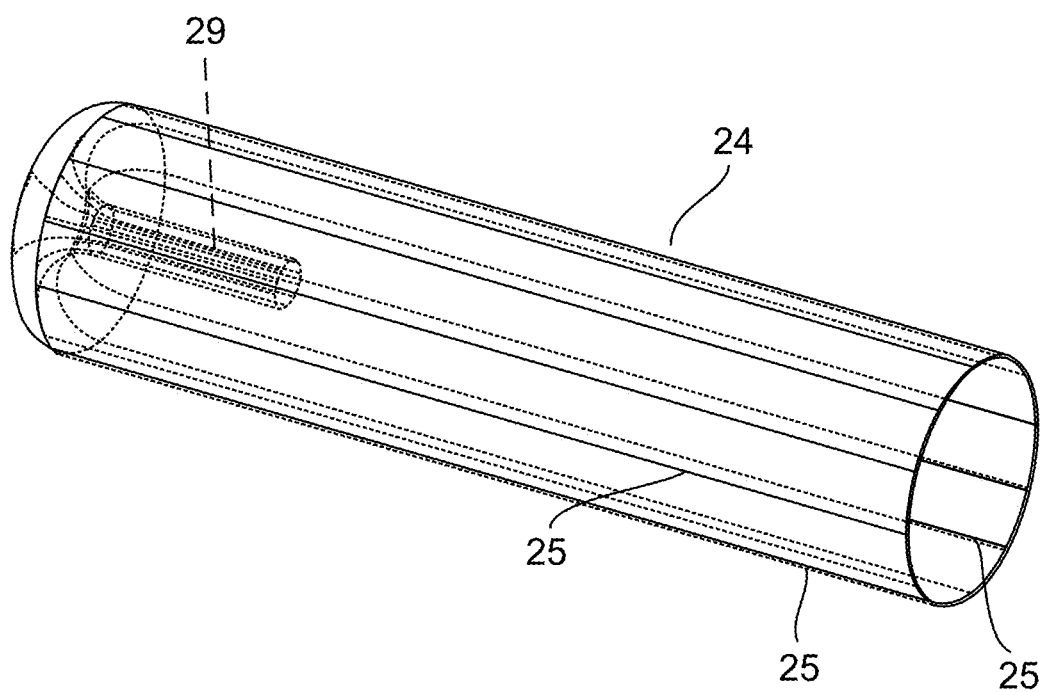
FIG. 2b illustrates the tubular cover with attached/integrated longitudinal struts.

The longitudinal rigidity of tubular cover 24 is provided by longitudinal reinforcement, e.g. axial elements, such as struts 25 which are attached to, or integrated into tubular cover 24 (FIG. 2b). Struts 25 can be embedded into tubular cover 24 during manufacturing (dipping, over molding) or joined thereto via gluing, sandwiching (dual layer) or the like. Struts 25 can be attached to distal connector 29 of tubular cover 24 which is in turn connected to (glued/welded) inner tube 14.

Any number of struts 25 can be provided in or on tubular cover 24. For example, 4-8 struts spanning the length of tubular cover 26 can be arranged around the circumference thereof in symmetrical or non-symmetrical spacing. Struts 25 can span the entire length of tubular cover 26 or a portion thereof (e.g. 70-95%).

Struts 25 can be configured to provide longitudinal rigidity only under pulling forces, since tubular cover 24 is pulled to uncover the delivered device. As such, struts 25 can be fabricated as strings (single filament of braided), or ribbons from inelastic polymers such as nylon, PLA or PEEK, or from natural materials such as silk or cotton. Struts 25 can also be fabricated from rigid materials such as, alloys (stainless steel) and the like. The axial compliance of struts 25 is less than 20%, preferably less than 10%.

Figure 4:
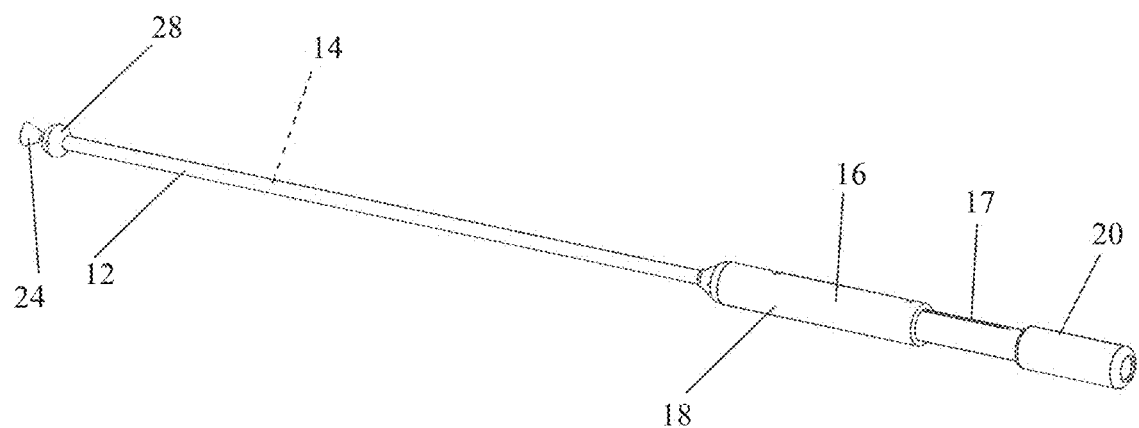
FIG. 4 illustrates the delivery apparatus of FIG. 1 with the tubular cover drawn into the lumen through the distal opening of the elongated (outer) tube.

FIG. 4 illustrates apparatus 10 without device 15 and with tubular cover 24 partially withdrawn into outer tube 12 showing distal portion 13 and nose cone 28. Nose cone 28 is shaped to facilitate delivery of apparatus 10 into the hollow organ and to enable easy retraction thereof. In addition, nose cone 28 also facilitates collection of tubular sheath (which slides thereupon) into outer tube 12. Nose cone 28 is preferably fabricated from low friction materials such as Teflon or Delrin. Nose cone 28 also functions as a distal stop to prevent any distal movement of the device carried on outer tube 12 during unsheathing of tubular cover 24.

FIG. 5 illustrates apparatus 10 with tubular cover 24 partially covering device 15 mounted on outer tube 12 and a conduit 30 disposed between handle 16 and distal portion 13. Conduit 30 includes a proximal opening 32 and distal opening 34. Conduit 30 can be used to deliver a friction reducing compound to distal portion preferably under tubular cover 24 within a space between tubular cover 24 and device 15. Such a friction reducing compound can be water or oil-based and can include glycerin and hydroxyethyl cellulose lubricants.

Delivery of the friction reducing compound can be facilitated by a syringe or pump connected to proximal opening 32 via, for example, a Luer lock mechanism. When delivered under tubular cover 24, the friction reducing compound can decrease friction caused by contact of inner walls of tubular cover 24 and outer walls of device 15 to thereby facilitate unsheathing of device 15 (via withdrawal of tubular cover 24 into outer tube 12). Delivery of the friction reducing compound can be effected prior to positioning of apparatus 10 carrying device 15 in the hollow organ, or following such positioning and prior to pulling of inner tube 14 with respect to outer tube 12.

Apparatus 10 can be used to deliver any intraluminal device into any hollow organ. One preferred device deliverable by apparatus 10 is the anastomosis bypass device described in U.S. Pat. No. 8,690,817 and generally shown in FIGS. 1, 3 and 5.

Such a device is a tubular sleeve constructed from silicone, PTFE, Dacron™ or latex or any other suitable material and having dimensions in the range of 250-500 mm length, 25-50 diameter and 0.05-1 mm wall thickness.

As is further described herein under, the movement of the tubular sleeve within the hollow organ (specifically downstream movement) is limited via an externally mounted movement-limiting element which is preferably configured as a band loosely encircling the hollow organ.

The sleeve includes an upstream opening for receiving the biological material transported through the hollow organ and downstream opening which serves as an exit point for the biological material.

The sleeve can include two distinct functional portions. A first (distal) portion functions in stabilizing the sleeve within the hollow organ and sealing it with respect to the hollow organ inner walls, thus serving as the entry portion for the biological material. The first portion is preferably more rigid in nature and can be shaped to facilitate movement of the biological material from the hollow organ and into the sleeve. The first portion of the sleeve is preferably constructed from silicone (Shore A 30-80), with a thickness of 0.1-0.6 mm and configured with an external diameter of 30-60 mm, and a length of 25-100 mm. This portion can also include stabilizing struts and inflatable external balloons for anchoring and stabilization. Although the diameter of the first portion can increase slightly under internal pressure exerted by passage of biological material, such increase is typically no more than 5-15% of the fully open diameter.

A second (proximal) portion of the sleeve can function in directing the biological material moving through the sleeve into a portion of the hollow organ downstream of the anastomosis site and/or outside the body. As such, this portion of the sleeve is designed to contain the biological material while providing some accommodation for volume and movement. The second portion of the sleeve can be elastic and flimsy and is preferably constructed from a silicone material (Shore A value of 5-40) and a thickness of 0.05-0.3 mm. Depending on the anastomosis location along the colon the second portion of the sleeve can range in length from 150-450 mm and 20-40 mm in diameter when fully open. For example, when utilized in bypassing a low colorectal anastomosis, the second portion of the sleeve can be 150-350 mm in length when fully deployed.

The first portion is preferably contiguous with the second portion and is thus fabricated as one unitary structure or assembled from two irreversibly attached portions (using for example, adhesives, mechanical fasteners and the like) which are assembled prior to positioning.

The first portion can also include a mechanism for further stabilizing the sleeve in the hollow organ and limiting its movement against the externally mounted movement-limiting element.

Such a mechanism can include an expandable structure which can be used for increasing the external diameter of the first portion following deployment. Examples include, stent-like bands which are expanded following deployment, compressed foam-like elements (disposed as a ring or discrete 'blocks' around the outer circumference of the first portion).

Expansion of such mechanisms can be effected by releasing a constraining mechanism such as a sheath or a pull-string. For example, a stent like band (cut out of a Nitinol or stainless steel tube or braided from Nitinol or stainless steel wire) initially shaped to about 50 mm outer diameter (OD) is compressed into a sheath with 10 mm internal diameter (ID); once released from the sheath, the stent-like band will elastically expand to the original 50 mm diameter.

A presently preferred expandable structure includes one or more (e.g. 2 or 3) inflatable structures (balloons/bladders/sacs) disposed as a ring (e.g. toroidal balloons) or a plurality of discrete inflatable structures around the outer circumference of the first portion.

Inflation of such an inflatable structure can be effected via an inflation conduit disposed within a sidewall of the sleeve. Depending on the anastomosis bypassed, such conduit can run the length of the sleeve from the distal opening to the inflatable structure(s), or it can traverse only a portion of this length (e.g. 100-400 mm).

As is mentioned above, the system of the present invention also includes a movement-limiting element for limiting the movement of the sleeve and preventing the first portion thereof from migrating past the anastomosis site (in a direction of flow through the hollow organ).

The presently preferred configuration of a movement-limiting element is a band encircling the outer surface of the hollow organ. It will be appreciated that such a band need not completely encircle the hollow organ; as such it can be an open band covering, for example, about 270 degrees of the circumference of the hollow organ.

A presently preferred configuration of the band is configured such that no substantial radial force is applied to the hollow organ when in use. Such a configuration negates the possibility of tissue ischemia and necrosis especially when the hollow organ is, for example, a colon which distends when fecal matter passes there through.

A hollow organ such as a colon is designed to radially expand in order to accommodate passage of feces during peristalsis (about 3-4 times per day). Such expansion can increase the diameter of a colon from 3 to 6 cm. A band positioned in close contact with the outer wall of the colon can apply inward pressure on the wall tissue when the colon expands during passage of feces. Such pressure can lead to tissue ischemia and necrosis and or to tissue erosion dues to both compressive forces and axial forces and frictional forces that result from axial movement of the colon with respect to the band.

To solve this problem, the band of the present invention can be configured to closely encircle the hollow organ and elastically expand when the organ expands, or alternatively and preferably the band can be configured with a diameter slightly smaller than that of the expanded organ (e.g. about 15-30% smaller), but larger than that of the relaxed state of the hollow organ (e.g. about 15-30% larger). In the case of colon anastomosis, the band can be fabricated with an internal diameter of 30-50 mm and a substantially rigid (e.g. 10% compliance) internal circumflex. Since the distal portion of the (internal) sleeve is relatively rigid (as described above), it may limit organ radial expansion at the site around and distally to the anastomosis and thus reduce contact forces/pressures between the organ outer wall and the band inner diameter.

The band limits movement of the sleeve (specifically the first portion of the sleeve) by functioning as a stop for the first portion of the sleeve (e.g. a stop for the balloon or balloon inflated around the first portion of the sleeve).

For example, a band having an internal diameter of 40 mm would function as a movement stop for a sleeve which includes a first portion having an external diameter of 50 mm and yet such a band would not apply compressive forces to the outer colon wall.

In order to limit migration of the sleeve downstream past the anastomosis site, the band is preferably located at or above the anastomosis site. To prevent migration, the band is secured to the tissue at the desired site via anchors, adhesive, sutures and the like. Such securement can be to the outer wall of the hollow organ or to tissues adjacent thereto. In the case of colorectal anastomosis, the band can be located about 50-100 mm above (upstream) the anastomosis and axially secured in place by threading the band through the colon mesentery.

The band is delivered as a linear strip and closed to a circle around the hollow organ using, for example, a latch, a suture, a lasso suture around the band or other locking mechanisms. Delivery of the band is preferably effected through an incision in the abdominal wall. The diameter of the band can be adjustable prior to or following positioning using, for example, a ratchet concept in which the relatively stiff outer rim of the band is tuned and locked to a diameter that will allow the above defined gap between the colon and the internal "relatively soft" inner band material or a Lasso concept in which the diameter of the ring is limited (and changed) by a "suture" going around the soft inner ring material. In that concept shortening of the suture length will decrees the ring OD.

According to another aspect of the present invention there is provided a method of delivering a device into a hollow organ using apparatus 10.

Delivery of a device 15 into a hollow organ using apparatus 10 is exemplified by FIGS. 6a-6h which illustrate delivery of an anastomosis bypass device into a colon.

Figure 6A:
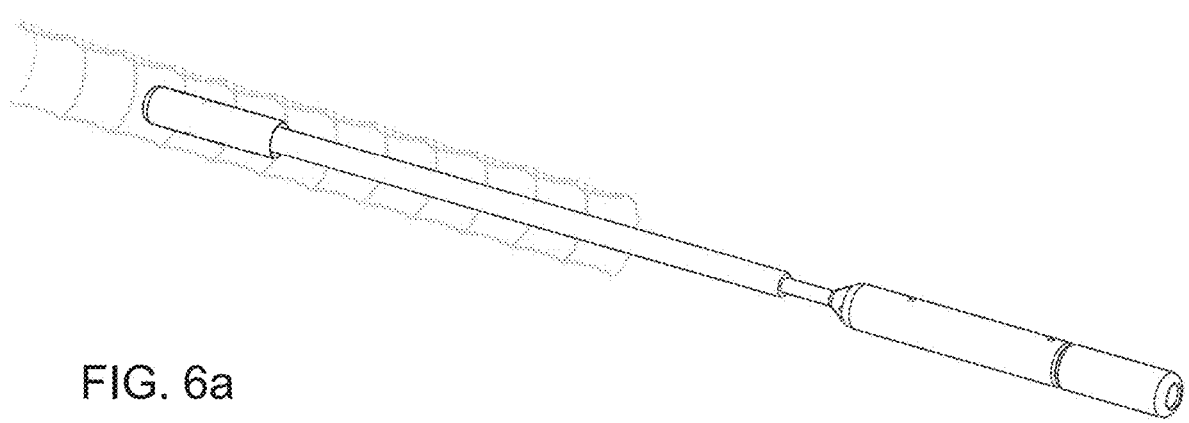
FIGS. 6a-6h illustrate delivery and deployment of an intraluminal device in a colon using the delivery apparatus of the present invention.
Figure 6B:
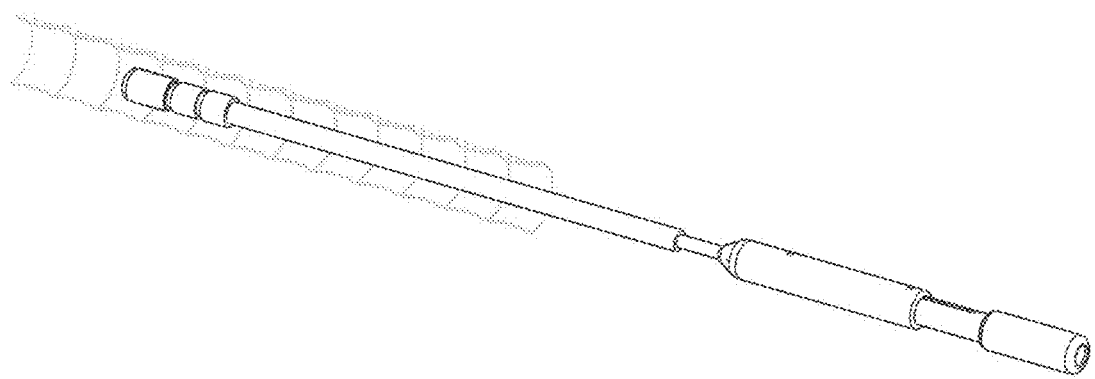
Figure 6C:
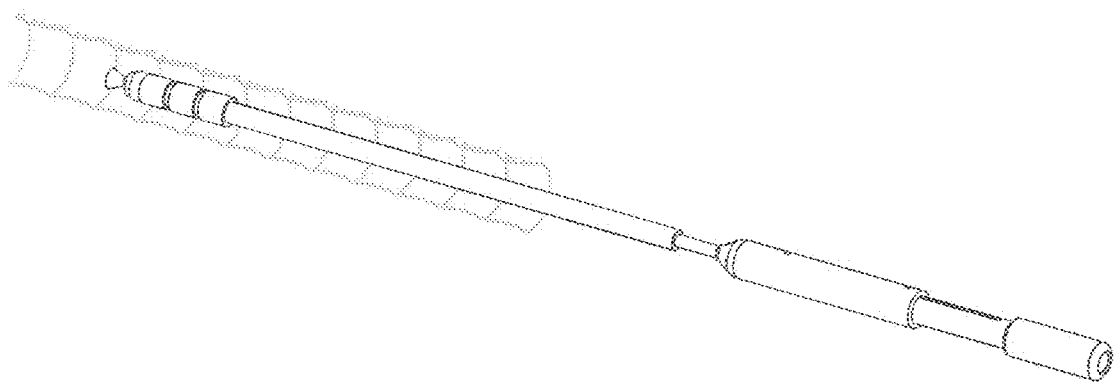
Figure 6D:
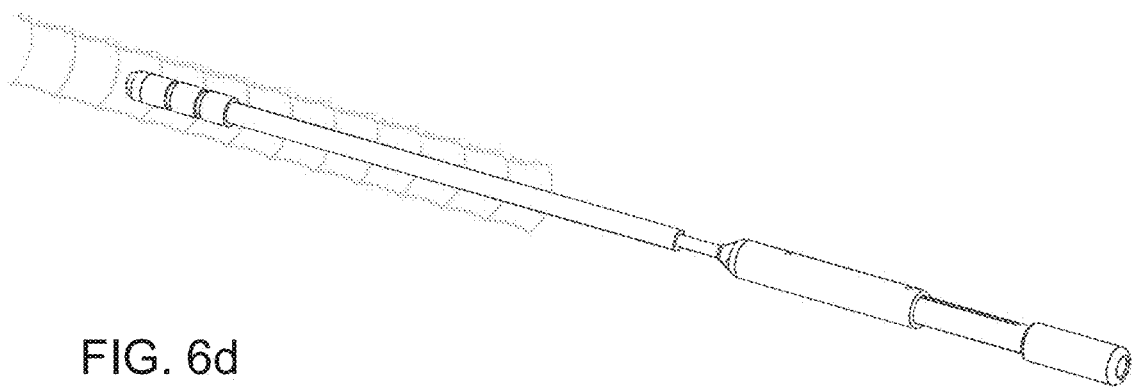
Figure 6E:
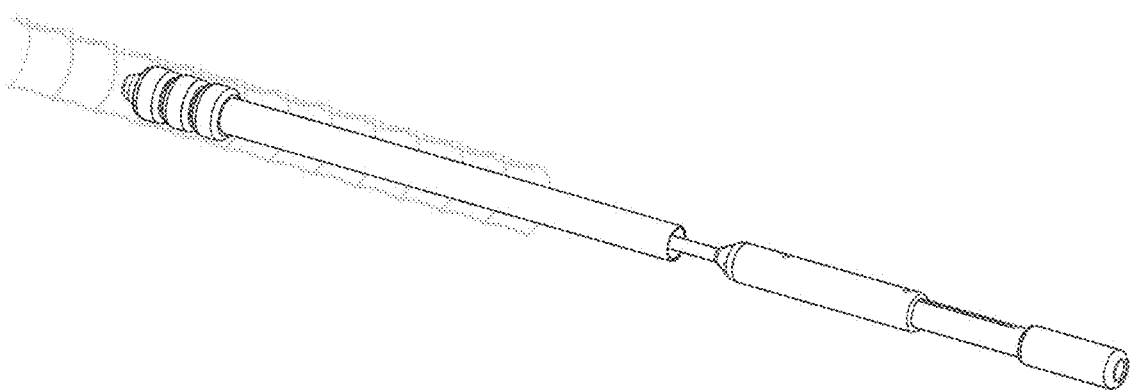
Figure 6F:
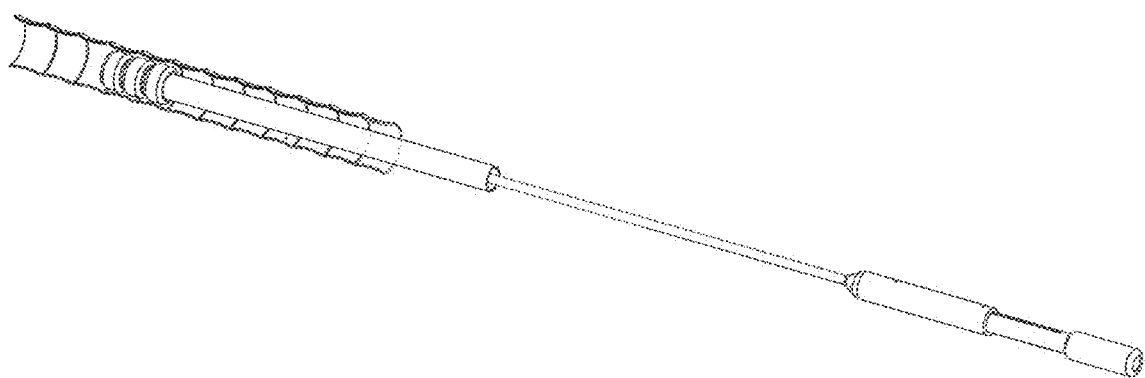
Figure 6G:
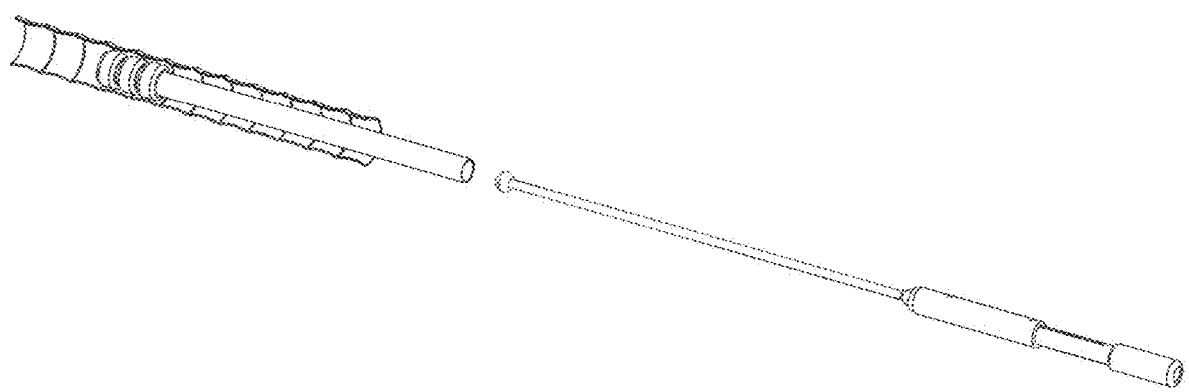
Figure 6H:
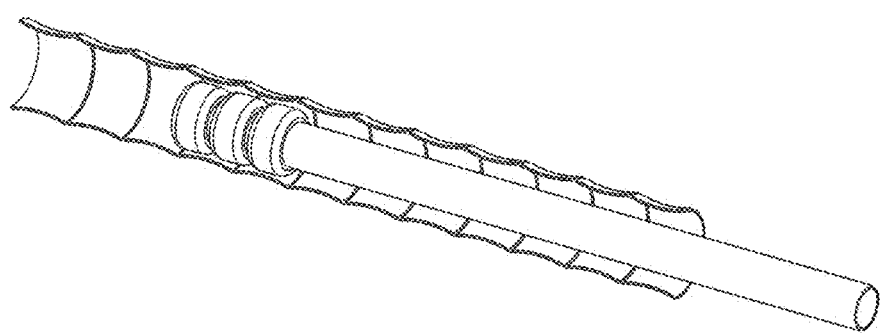

Apparatus 10 with a mounted device is inserted through the anus and advanced to the anastomosis site until the distal end is located proximal to the external ring (FIG. 6a). A safety pin locking portion 20 to portion 18 is removed and the handle is pulled proximally withdrawing the tubular cover and exposing the device (FIGS. 6b-6d). Starting with the proximal balloon, each balloon of the device is inflated with 15 ml of saline using a standard 20 ml syringe positioned outside the body (FIG. 6e). Once the balloons are inflated, apparatus 10 is completely withdrawn from the colon/rectum via gentle pulling (FIGS. 6f-6g) leaving the device anchored in position in the colon (FIG. 6h).

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Animal Testing

A delivery apparatus prototype constructed having an elastic tubular cover was evaluated in pigs.

Figure 7:
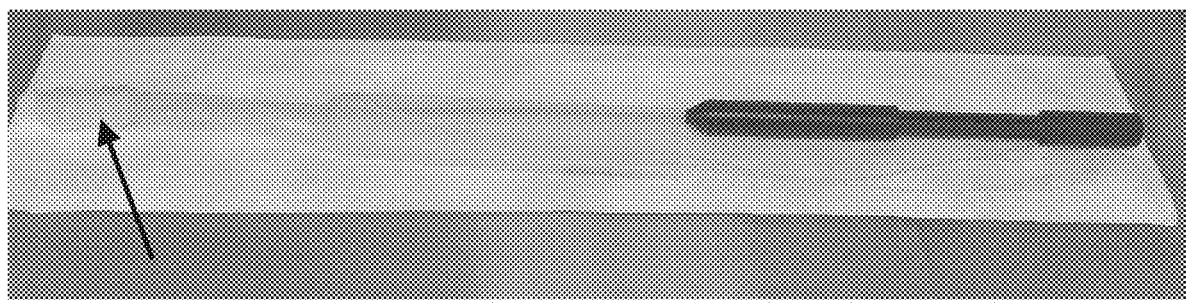
FIG. 7 illustrates a prototype of a delivery apparatus which includes a longitudinally elastic tubular cover. As is shown by this Figure, pulling of handle proximally stretches the tubular cover longitudinally and prevents release of the device from the delivery apparatus.

Uncovering the delivered device by pulling the elastic cover into the elongated tube proved extremely difficult due to high frictional forces between the tubular cover and device and colon. When the handle was pulled proximally, the tubular cover stretched longitudinally (axially) and remained in position (FIG. 7 illustrates a deployed delivery apparatus outside the body, stretched cover indicated by arrow) preventing release of the device from the delivery apparatus.

To traverse this limitation of an axially elastic tubular cover, the present inventors fabricated an improved prototype having a tubular cover which is radially elastic and longitudinally inelastic. This improved prototype was evaluated in 16 animal trials (pigs) and results showed that the tubular cover was easily withdrawn into the elongated outer tube of the apparatus to uncover the device and enable delivery thereof.

Example 2

Human Testing

Figure 8:
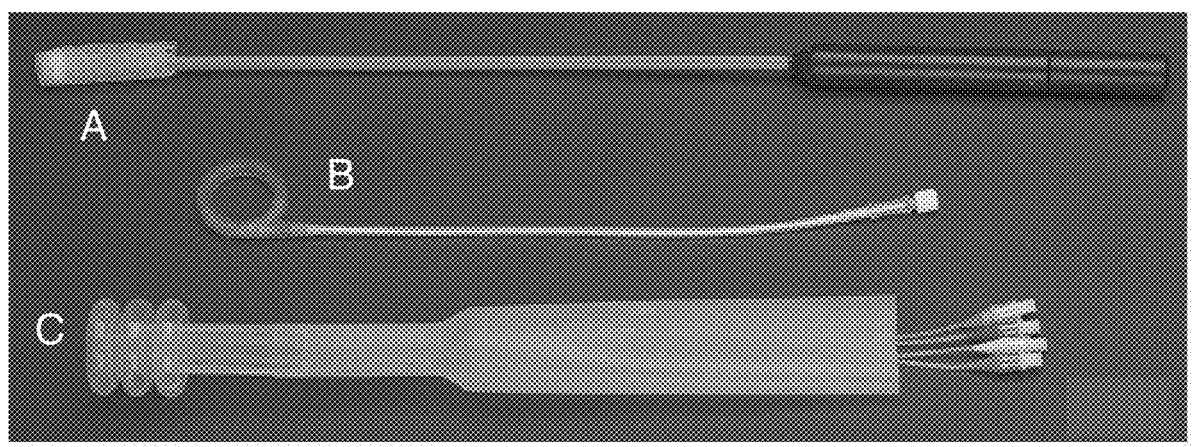
FIG. 8 illustrates a prototype system including a delivery apparatus (A), a movement limiting band (B) and anastomosis shield device (C).

A prototype of the present delivery device was tested in human subjects (FIG. 8). A single arm open label study was conducted in order to evaluate safety, tolerability and performance profile of the present delivery apparatus and the intraluminal device delivered thereby (described in U.S. Pat. No. 8,690,817) in patients undergoing colorectal surgery.

The objectives of this study were to assess the performance of the delivery apparatus and the device delivered thereby.

Methodology

A total of 14 subjects (7 males/7 females) were enrolled and completed 30 days follow up to date. A single subject (female) was excluded from the study due to failure of leak test.

Subjects were scheduled for elective colorectal surgery as per the site standards. The device was deployed in the anastomosis site as follows.

Briefly, the external ring/band (B) was positioned around the colon upstream of the anastomosis site during the open part of the procedure when the resected bowel was pulled out of the abdominal wall through a small incision. The delivery apparatus (A) with a mounted device (C) was inserted through the anus and advanced to the anastomosis site until the distal end of the delivery apparatus was located upstream of the external ring (B). The handle of the delivery apparatus was unlocked and pulled proximally to withdraw the tubular cover and expose the device. Starting with the proximal balloon, each balloon of the device was inflated with saline using a standard 20 ml syringe positioned outside the body. Once the balloons were inflated, the delivery apparatus was completely withdrawn from the colon/rectum via gentle pulling leaving the device anchored in position in the colon.

All variables concerning the procedure were collected including duration of the entire procedure, additional time for application of the device, inspection of the donuts, and whether a diverting stoma had been created.

In 13 patients (7 men, 6 women) a low colorectal resection was performed. The indication for treatment in all patients was colon and rectal cancer. The average age of the patients was 65 years (range, 51-83 y). Subjects' BMI ranged from 20 to 32 with average of 27.9. Preoperative neo-adjuvant chemo radiotherapy had been given to 6 patients.

Type of surgery was diverse and included 2 open surgeries, 9 laparoscopic surgeries, 1 Robotic surgery converted to open and 1 robotic converted to lap. In all cases, delivery of the device was through the anal orifice.

The average duration of the surgical procedure was 231 minutes (range, 125-332 min). Application and deployment of the device added a median of 7 minutes to the procedure (range 5-21 min). The median distance from the anal verge to the anastomosis was 5 cm (range, 2-14).

In 6 of the procedures, a diverting stoma was created in addition to the placement of the device. Device removal was performed per protocol on day 9-11 post procedure for 12 subjects. Early removal was performed in one patient on day 4 (subject 03-02) due to leakage from the anastomosis site.

Post-surgery activities included a daily evaluation of subject's clinical state and assessments/record of temperature, passing flatus and bowel movements, concomitant medications (with focus on laxative, antibiotics, parenteral narcotics, or oral analgesic), food intake tolerability (liquid/solid) and catheter use.

On Day 10 (±1), a rectal contrast enema was done according to institution standard technique to determine device positioning and integrity of the anastomosis, followed by device removal.

Approximately 30 (±5) days post-surgery, subjects returned to the clinic/hospital for a long-term follow-up safety evaluation of adverse events, physical examination (digestive system) and concomitant medications.

Results

Delivery was evaluated by the surgeon using feedback questionnaire. Answers were evaluated using a 5 point scale, with 1=must improve, and 5=Excellent. Average scores are detailed in the Table below.

TABLE 1

Surgeon Feedback - Device Usability

| | | Average score | Definition |
|---|---|---|---|
| 1 | Learn-ability of the technique (compared to other systems) | 4.67 | Intuitive/ Memorable |
| 2 | Overall level of complexity of the device (general) | 4.17 | Clear |
| 3 | Device ease of use | 4.17 | Fairly easy |
| 4 | Compatibility and adequacy of device design to anatomy | 4.08 | Good |
| 5 | Device external ring deployment | 4.33 | Good |
| 6 | Device internal sheath deployment (including positioning & balloons inflation) | 4.08 | Good |
| 7 | Withdrawal of the delivery system after deployment | 4.25 | Good |
| 8 | Fixation of external ring connecting tube | 4.50 | Excellent |
| 9 | Fixation of inflation tubes | 4.33 | Good |
| 10 | Removal of external ring | 4.42 | Good |
| 11 | Removal of internal sheath | 4.33 | Good |

Overall device usability was found to be very good (average score 4.3). The physicians found it to be simple, clear and easy to use throughout all stages of deployment and removal.

The application of the device can be performed easily by any surgeon experienced in colorectal anastomoses procedures, with median application time of 7 minutes (5-21) vs. stoma formation 15 minutes (10-30).

All subjects completed the study with no incidents of death or major complications such as septic shock, general peritonitis etc. Patients did not report major discomfort caused by the sheath. A minimal incontinence for loose stool was observed as long as the sheath was in situ.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

To the extent that section headings are used, they should not be construed as necessarily limiting. In addition, any priority document(s) of this application is/are hereby incorporated herein by reference in its/their entirety.

What is claimed is:

1. A method of treating a gastrointestinal tract comprising:
   (a) delivering into the gastrointestinal tract a device mounted one an elongated tube having proximal and distal openings, said device being a tubular sleeve having at least one toroidal balloon and being at least partially covered by a tubular cover being radially elastic and axially non-elastic;
   (b) retrieving said tubular cover into said elongated tube through said distal opening thereby uncovering said device; and
   (c) pulling said elongated tube in a proximal direction to thereby deliver said device to the gastrointestinal tract, wherein said toroidal balloon is inflated to anchor said tubular sleeve in the hollow organ prior to, or following (c).

2. The method of claim 1, wherein said tubular cover is attached to an additional elongated tube positioned within said elongated tube and further wherein (b) is effected by pulling said additional elongated tube against said elongated tube.

3. The method of claim 1, wherein said tubular cover is fabricated from an elastic material having non-elastic axial elements.

4. The method of claim 1, wherein said device is delivered in a colon and said tubular sleeve is at least 200 mm in length.

5. The method of claim 1, wherein (a) is effected by delivering said device through said anal orifice.

6. The method of claim 4, wherein said at least one toroidal balloon is inflated via an inflation conduit having an inflation port positioned outside the body.

7. The method of claim 1, further comprising delivering a friction-reducing composition to a distal portion of said elongated tube prior to (b).

8. The method of claim 7, wherein said delivering is effected via a fluid conduit having a distal opening positioned at said distal portion of said elongated tube.

9. The method of claim 8, wherein a distal opening of said fluid conduit is positioned such that said friction-reducing composition is delivered between said tubular cover and said device.

10. The method of claim 7, wherein said friction-reducing is an oil or a water-based lubricant.

11. The method of claim 1, wherein said device is fabricated from Silicone.

12. The method of claim 2, wherein said additional elongated tube is connected to handle having a safety mechanism for preventing said tubular cover from being pushed out once pulled into said elongated tube.

13. The method of claim 12, wherein said safety mechanism is a ratchet mechanism.

* * * * *